United States Patent [19]

Perren et al.

[11] 4,125,822
[45] Nov. 14, 1978

[54] PROBE FOR DETERMINING ORGANIC LIQUIDS

[76] Inventors: Benno Perren, Austrasse 33, CH-5430 Wettingen; Herbert Schreiber, Belvedere Str. 63, CH-8968 Mutschellen, both of Switzerland

[21] Appl. No.: 624,243

[22] Filed: Oct. 20, 1975

Related U.S. Application Data

[63] Continuation of Ser. No. 408,573, Oct. 23, 1973, abandoned.

[30] Foreign Application Priority Data

Oct. 23, 1972 [DE] Fed. Rep. of Germany ....... 2251952
Sep. 5, 1973 [DE] Fed. Rep. of Germany ....... 2344778

[51] Int. Cl.$^2$ ............................................. G01N 27/04
[52] U.S. Cl. ..................... 338/34; 23/230 L; 23/230 M; 324/65 R; 338/223; 422/69
[58] Field of Search ................. 324/65 R; 73/337; 23/230 L, 253 R, 230 R, 230 M; 338/34, 223

[56] References Cited

U.S. PATENT DOCUMENTS

| | | | |
|---|---|---|---|
| 2,589,983 | 3/1952 | Blodgett et al. | 73/337 X |
| 2,626,381 | 1/1953 | Olson | 324/65 R X |
| 3,295,088 | 12/1966 | Smith | 324/65 R X |
| 3,479,864 | 11/1969 | Patterson | 73/64.3 |
| 3,800,219 | 3/1974 | Fosberg | 324/65 R |

FOREIGN PATENT DOCUMENTS 1,179,024 10/1964 Fed. Rep. of Germany ............. 338/34

*Primary Examiner*—Morris O. Wolk
*Assistant Examiner*—Arnold Turk
*Attorney, Agent, or Firm*—Burns, Doane, Swecker & Mathis

[57] ABSTRACT

The presence of an organic liquid is detected by means of a probe which comprises a rubber-like material which is swellable in an organic liquid, which rubber-like material has electrically-conductive solid particles distributed therethrough, in such concentration as to touch each other.

2 Claims, 3 Drawing Figures

PROBE FOR DETERMINING ORGANIC LIQUIDS

This application is a continuation of applicants' prior application Ser. No. 408,573 filed Oct. 23, 1973 (now abandoned).

The invention relates to a probe for determining organic liquids, especially mineral oils and fuels, and also to the application of the probe in electrical measuring or alarm devices.

There is danger of leakages due to errors in operation or technical shortcomings wherever organic liquids such as solvents, mineral oils or fuels are being stored, possible explosions leading to often devastating consequences, same also being due to any water contaminations. Such jeopardized or endangered sites are for instance supply tanks, pipelines, oil burners, gas stations, pumping stations, reshipment points, industrial facilities and electrical facilities containing oils, or such driven by hydraulic means. The detection of leaking organic liquids so far has been feasible only by constant visual observation.

It is known how to make oil-swelling rubber electrically conducting by adding lampblack. However the conductivity so achieved is too low to make use of this rubber for monitoring purposes, especially where long probes are concerned.

The invention addresses the task of immediately determining even very minute quantities of organic liquids and even in the presence of long measuring segments and to render alarm feasible.

The solution of the invention as regards this task for a probe of the initially mentioned kind consists in making the probe of a material such as plastic or rubber which is soluble or will swell in organic liquids and wherein are contained solid particles with a surface electrical conductivity in the range of that of the metals, finely distributed and in such concentration as to touch each other.

The probe material is of relatively low electrical resistance which upon contact with organic liquids will increase by several decades toward infinity. Therefore the probe may be used in connection with a measuring device for electrical resistance or with a relay for initiating an alarm or a display.

The probe may be made as a strip or in wire form and laid out at the endangered sites. One may therefore monitor a large area at the same time. One embodiment is particularly advantageous, wherein the probe material is deposited as a thin layer on a strip of non-conducting stratum. Plates, foils, tissues, webs or synthetic papers may be used as substrates. One may also use threads or monofilaments as sleeving material for the probe.

Such substances as the polymerisates or mixed polymerisates of the higher methacrylic or acrylic acid esters, of olefins or alkadienes, especially butene, isobutene, butadiene and isoprene, are suitable as probe materials for monitoring mineral oils and fuels. They may contain natural or synthetic resins for reinforcing, or be slighty cross linked, or even form microgels.

The electrically conducting solid particles may be metallic powders. Iron, nickel, chromium, copper, but especially silver and its alloys are suitable. Metals forming insulating layers on their surfaces, for instance aluminum, are not suited.

Particularly suitable are solids metallized for instance with copper, chromium, gold, but especially silver on the surface of the individual particles. The inside of the particles need not be metallic and may be for instance stone powder, glass, or plastic. Metallized solids allow large savings in dear metals, yet provide the same high conductivity as the metal powders and similarly allow arbitrary shaping of the solid particles. It was found that the highest response is achieved from a combination of rod-like or leaf-like particles with spherical ones. Silvered microglass spheres or stone dusts and silvered glassfiber dust are suitable for such combinations.

The size of the solid particles may vary within wide limits. It will be of advantage to use diameters less than 1 mm, especially less than 0.1 mm. The size distribution should appropriately be as uniform as possible.

When properly designed and built, these probes are extensively insensitive to external forces, shocks, impacts etc. on account of the toughness of the materials. However they are highly sensitive to organic liquids and of short time-constants.

When such probes are immersed in water, they will not respond. Their application with respect to determining small amounts of organic liquids in water or to sensing thin oil or benzene layers on top of the water will fail because water-wetting the probe will keep hydrocarbons away from it. It will be wetted only by a fairly thick layer, and it will detect the presence of an organic impurity on account of swelling. The solubility of benzol, for instance, in water is about 800 mg/liter. Determining dissolved benzol in water when the probe is of normal design will not be possible on account of the slight concentration.

The probe may be made operative in both intances by adding simple accessories. Polytetrafluoroethylene, commercially known as teflon, is water-repellent, yet capable of binding even the most tenuous drops of hydrocarbons to its surface. Teflon also is dirt-repellent and no growth of organic life so far has been observed on it. If now the surface of the probe material is provided with a thin porous teflon layer, then even the least traces of, say, oil on top of the water, or oil droplets that may be in the water and accidentally come to touch the probe, will adhere to the latter's surface. The presence of the oil then is being signalled the moment the minimum amount required for causing swelling of the probe material has collected. Measuring the changes in electrical resistance of the probe allows inferences regarding the concentration of the contamination and latter's change with time. If porous teflon is used as substrate or is added to the probe material, the response sensitivity may be appreciably increased.

Obviously one may also use such substances which are less effective than teflon though endowed with essentially the same properties, for instance acetal resin, nylon or polypropylene.

In order to establish the presence of organic liquids dissolved in water, the probe material at least at its surface is made to react with an adsorber specifically responding to the particular impurity. Various substances are known, for instance active carbon, foamed vulcanic stone and most synthetic foams, that are capable of removing such contaminations 100% from the water. If now for instance fine-grained active carbon particles are being used, then they are capable of removing the dissolved organic liquids from the water and to pass them in part to the probe material. The moment there is sufficient concentration, the probe will respond.

Depending on the particular application, the probe material might be reacted only with active carbon additions or else also be provided with a porous teflon coating. If the surface of the active carbon grains is coated with a thin metal layer through which layer organic fluids can diffuse, then the active carbon assumes both the function of the adsorber & that of the solid electrically conducting particles in the probe material.

Such probes will not respond to pure water, not even after arbitrary long times in that water; on the other hand, they will respond virtually instantaneously to the presence of organic liquids if these are there in sufficient quantities. If such organic liquids are present only in the form of additions, the change in electrical resistance of the probe — as explained above — largely depends on the concentration of the impurities and on the time of exposure to these.

If the probe is used to determine the presence of organic impurities in water, then the presence of the latter becomes an irrevocable assumption as regards the operation of the probe. It may for instance be so designed as to deposit the swelling material on one side of the substrate and in making the other the conductivity-meter. One may for instance test the emersion of the probe out of the water by means of a separate circuit closed by the water, as well as the presence of water. However, the opposite case may also occur. If the probe meant to detect a storage tank leak is totally submerged by water, it will be incapable of determining any leaking oil. Therefore water detection is appropriate.

EXAMPLE

Synthetic paper with a lacquer coating about 1 mm thick and of 10 gm poly-cis-1,4-butadiene, 30 gm silvered quartz powder with 0.01 - 0.04 mm grain diameter and 100 gm toluol is cut into 5 mm wide strips following drying. A strip 1 meter long has a resistance of about 500 ohms. If a drop of heating fuel is deposited on one place on the strip, the resistance increases within 10 seconds to beyond 10 megohms.

The invention will now be further described in the following, taken with the appended drawings, in which.

Figure 1:
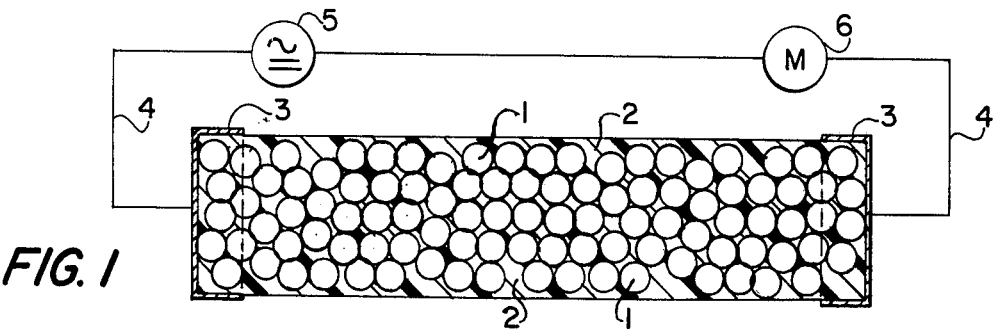
FIG. 1 is a diagrammatic representation of a probe in accordance with the present invention.

In FIG. 1, the probe is seen to comprise a body consisting essentially of electrically-conductive solid particles 1 which are distributed through a mass of oil-swellable rubber particles 2. Said body, in the form of a strip, is provided with electrically conductive terminal connections 3, 3, at the oppoite ends of the body, which terminal connections are brought into a circuit including battery means 5 and meter 6 by way of electrical conductors 4. 4.

The probe thus diagrammatically represented may consist of a dispersion of silvered quartz powder dispersed through a body of butadiene rubber encased in a lacquer coated synthetic paper tube as described in the above Example. The probe is sensitive to the presence of a very small amount, e.g., a drop, or two, of fuel oil, the presence of which causes an increase in the resistance of the body to the very substantial extent described in said Example.

Figure 2:
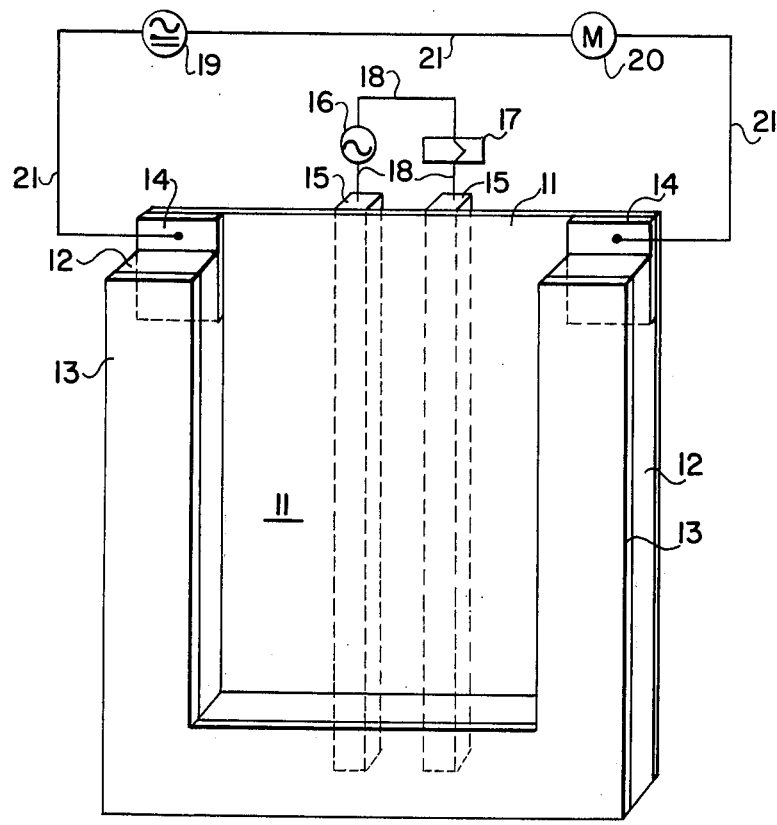
FIG. 2 is a diagrammatic showing of a complete installation including the probe of the invention.

In FIG. 2, the aforesaid U-shaped oil probe 12 is shown in position in a a system which includes a layer 13 of a material that facilitates collection of organic liquid. The system comprises a support 11, the aforesaid U-shaped oil probe 12 being a swellable layer of rubber-like material having electrically-conductive solid particles distributed therethrough, and conventional junctions 14, 14, to which conductors 21, 21 are fixed. The two probes 15, 15 which measure the conductivity of a liquid to be tested, are positioned at the side of support 11. An electrical measuring unit or control circuit is formed by an a.c. voltage source as shown at 16 and a highly sensitive relay at 17, which source and relay are in communication with conductivity probes 15, 15 by way of electrical conductors 18, 18.

Evaulation of the current detected in the probe system above described is effected by the circuit including a voltage source 19, electric meter 20 and the aforesaid conductors 21, 21 secured to the junctions 14, 14.

Figure 3:
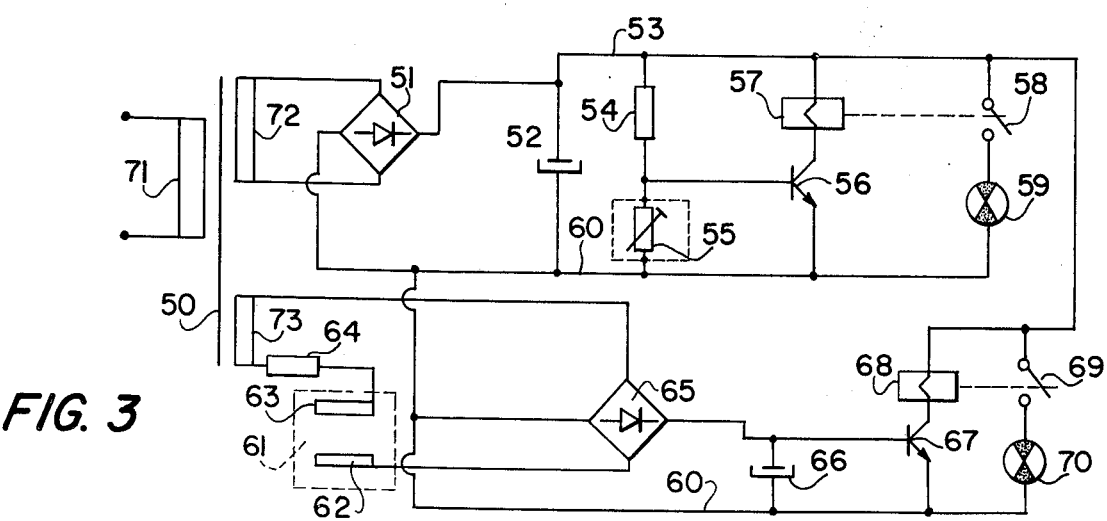
FIG. 3 is a wiring diagram for an electrical alarm system employing the probe of the invention.

FIG. 3 shows an electrical circuit diagram of the arrangement wherein the upper portion of the circuitry depicts an evaluation circuit of an oil probe whilst the lower portion shows circuitry of a probe measuring conductivity, such circuitry of an alarm system including a probe 55 in accordance with the present invention, the resistance of which probe is measured in the system shown in the diagram.

In this system, a power transformer is represented at 50, in which 71 consists of a primary winding and secondary windings 72, 73. Secondary winding 72 is connected to opposite poles of a wheatstone bridge rectifier 51. Part 52 is filter capacitor which is electrically connected to the other poles of bridge 51 through a positive voltage feed 53 and a negative voltage feed 60.

Probe 55 and an associated resistance 54 are in electrical communication with 53, 60, and also with a transistor 56 which latter is electrically connected through a relay 57 and contact 58 with one junction point of an indicator lamp or alarm 59. Negative voltage feed 60 is connected to the other junction point of said indicator.

A probe for measurement of electrical conductivity is represented at 61 and electrodes 62, 63. Electrode 63 is connected to secondary winding 73 by way of a current-limiting resistor 64, whilst electrode 62 is connected to one pole of a wheatstone bridge rectifier 65, one of the non-opposite poles (with respect to the electrode 62-connected pole) of which is in communication with a charge condenser 66 and also with a transistor 67.

Negative voltage feed 60 is in electrical connection with the other of the above referred-to non-opposite poles of bridge 65. Part 68 is a relay associated with an indicator lamp 70 through a contact 69.

With the conductivity-measuring probe 61 immersed in water, the voltage across the capacitor 66 will rise to such value that the transistor 67 becomes modulated and the relay 68 activated. When the conductivity-measuring probe emerges from the water, for example, if the water recedes, the alternating voltage across the rectifier 65 and the direct current across the capacitor 66 will drop practically to zero; the transistor 67 will cut out, the relay 68 will drop and close with its contact 69 the circuit of the pilot lamp 70, or of an alterting unit, repsectively, of the conductivity-measuring probe.

I claim:

1. A probe for determining the presence of mineral oil, which comprises:
   a plastics material which is swellable on contact with mineral oil, and
   solid particles finely distributed through said material and present therein in such concentration as to touch each other, said solid particles being less than 1.0 mm in diameter and having a surface conductivity of the order of a metal, at least at the surface thereof the probe comprises an adsorption material having a preferential attraction toward mineral oil.

2. A probe as defined in claim 1, wherein the adsorption material consists of grains of active carbon having a thin metallic deposit on surfaces thereof.

* * * * *